United States Patent [19]

Johnson

[11] 4,455,427

[45] Jun. 19, 1984

[54] PYRIDYL-SUBSTITUTED-BENZOFURANS

[75] Inventor: Roy A. Johnson, Brookline, Mass.

[73] Assignee: The Upjohn Company, Kalamazoo, Mich.

[21] Appl. No.: 430,293

[22] Filed: Sep. 30, 1982

Related U.S. Application Data

[63] Continuation-in-part of Ser. No. 385,622, Jun. 8, 1982, abandoned, which is a continuation-in-part of Ser. No. 279,374, Jul. 1, 1981, abandoned.

[51] Int. Cl.$^3$ .............................................. C07D 405/12
[52] U.S. Cl. ..................................... 546/269; 546/270
[58] Field of Search ................................ 546/269, 270

[56] References Cited

U.S. PATENT DOCUMENTS 4,112,224  9/1978  Bundy ................................. 542/426
4,259,338  3/1981  Paioni et al. ....................... 424/267

FOREIGN PATENT DOCUMENTS 50297    5/1982  European Pat. Off. .
2537837  3/1976  Fed. Rep. of Germany .
2039903A 8/1980  United Kingdom .

OTHER PUBLICATIONS

D. Harris, et al., Advances in Prostaglandin and Thromboxane Research 6:437 (1980).
T. Miyamoto, et al., Advances in Prostaglandin and Thromboxane Research 6:443 (1980).
H. Tai, et al., Advances in Prostaglandin and Thromboxane Research 6:447 (1980).

*Primary Examiner*—Henry R. Jiles
*Assistant Examiner*—Bernard Dentz
*Attorney, Agent, or Firm*—Lawrence T. Welch

[57] ABSTRACT

The present invention provides novel pyridinyl-benzofurans and derivatives thereof which are useful as thromboxane $A_2$ ($TXA_2$) inhibitors and as such represent potent pharmacological agents.

10 Claims, No Drawings

PYRIDYL-SUBSTITUTED-BENZOFURANS

CROSS REFERENCE TO RELATED APPLICATIONS

This application is a continuation in part of copending application Ser. No. 385,622, filed June 8, 1982 now abandoned, which is a continuation in part of Ser. No. 279,374, filed July 1, 1981, now abandoned.

BACKGROUND OF THE INVENTION

The present invention relates to novel compositions of matter. More particularly, the present invention relates to pyridyl substituted benzofurans. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift No. 2,537,837.

SUMMARY OF THE INVENTION

Thus, the present invention particularly provides: a compound of the formula I wherein $Z_1$ is
(a) 4-pyridinyl,
(b) 3-pyridinyl, or
(c) 3-pyridinyl substituted at the 4 position by
  (1) methyl,
  (2) —$OCH_3$,
  (3) —$N(CH_3)_2$, or
  (4) $NH_2$, or
(d) 3-pyridinyl substituted at the 2, 4, 5, or 6 position by chlorine;
wherein $X_1$ is
(a) —O—,
(b) —S—,
(c) —S(O)—,
(d) —$S(O)_2$—,
(e) —$CH_2$—$N(R_3)$—, or
(f) —$N(R_3)$—$CH_2$—,
wherein $R_1$ is hydrogen, a pharmacologically acceptable cation, ($C_1$-$C_{12}$) alkyl, ($C_3$-$C_{10}$) cycloalkyl, ($C_7$-$C_{12}$) aralkyl, phenyl, phenyl mono-, di-, or trisubstituted by chloro, ($C_1$-$C_3$) or alkyl, or phenyl para-substituted by
(a) —NHCO—$R_{25}$,
(b) —O—CO—$R_{26}$,
(c) —CO—$R_{24}$,
(d) —O—CO—(p-Rh)—$R_{27}$, or
(e) —CH=N—NH—CO—$NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein —(p-Ph) is 1,4-phenylene;
wherein $R_7$ is
(a) hydrogen,
(b) —$CH_2OH$,
(c) —$COOR_1$,
(d) —$CH_2N(R_4)_2$,
(e) —CN
(f) —$CON(R_4)_2$, or
(g) —C(O)—$R_4$;
wherein $R_3$ is
(a) hydrogen,
(b) ($C_1$-$C_3$)alkyl, or
(c) acyl;
wherein $R_4$ is
(a) hydrogen,
(b) ($C_1$-$C_4$)alkyl, or
(c) phenyl;
wherein $R_9$ and $R_{12}$ are the same or different and are
(a) hydrogen,
(b) ($C_1$-$C_4$)alkyl
(c) fluoro,
(d) chloro,
(e) bromo,
(f) —$OCH_3$, or,
(g) when taken together and attached to contiguous carbon atoms, —O—$CH_2$—O—;
wherein D represents a single or a double bond; and
wherein m is an integer from 0 to 4, inclusive; including, pharmacologically acceptable acid addition salts thereof; and
when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$-$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as benzofurans, using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, one compound, 5-(3-pyridinyloxy)benzofuran-2-carboxylic acid, sodium salt (Example 5), has been shown to be the most effective in inhibiting $TXA_2$ formation. This compound has an approximate $ED_{50}$ in this system of between 10 and 100 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 500 μg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Charts A-K.

Thus, the compounds of the present invention wherein m is zero are prepared by the method of Chart A. In Chart A, $R_{10}$ is all substituents within the scope of $R_1$ excluding the pharmacologically acceptable cations. All other variables in Chart A are defined as above. A hydroxybenzaldehyde of the Formula X is cyclized into the compounds of the present invention by methods known in the art. See, e.g., S. Tanaka, J. Am. Chem. Soc., 73:872 (1951). Thus, the compound may be reacted with diethyl bromomalonate in the presence of potassium carbonate to yield the desired benzofuran-2-carboxylic acid ester. See, e.g., D. T. Witiak, et al., J. Med. Chem. 21:833 (1978). Higher yields are obtained when the reaction conditions are changed so that the compound is reacted in the presence of sodium hydride in toluene (solubilized with dicyclohexyl-18-crown-6). Conversion of the ester of the Formula XV to the desired pharmacologically acceptable salts or free acid is accomplished by known methods.

The compounds of the Formula X are well known and readily available compounds, and may be prepared from known benzylpyridines of the Formula XX as depicted in Chart B. (See, also, British patent application No. 2,039,903A.)

Referring to Chart B, a compound of the Formula XX, wherein all variables are defined as above, is nitrated by methods well known in the art, for example, treatment with nitric acid. (While the para nitro compound is the predominant product, the meta and ortho nitro compounds are also formed in smaller quantities. The desired isomer is separated by known methods.) The nitro function is easily reduced by treatment with hydrogen over a 5% palladium-on-carbon catalyst, to form a Formula XXII amine. This amino group is replaced by a hydroxyl moiety via diazotization followed by decomposition of the diazonium salt in hot aqueous acid. Formylation of this phenol to obtain the hydroxybenzaldehyde of the Formula XXIV is accomplished by modification of the Duff reaction (see. J. Duff, J. Chem. Soc. 547 (1941)), by the use of hexamethyltetramine in trifluoracetic acid, see, W. E. Smith, J. Org. Chem., 37:3972 (1972).

Compounds of the Formula XX when $X_1$ is —CH$_2$N— may not be readily available. However, compounds of the Formula XXIII when $X_1$ is —CH$_2$N— are disclosed in G. Walker, et al., J. Med. Chem. 9:624 (1966). Formula XX compounds when $X_1$ is —O— are disclosed in F. Villani, et al., J. Med. Chem. 18:1 (1975).

For compounds wherein m is one, the method of Chart C is used. An ester of the Formula XL is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII products. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart D depicts the synthesis of compounds of the present invention wherein m is 2, 3, or 4. In Chart D, q is zero, one, or 2. An ester of the Formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formula Ph$_3$P=CHCH$_2$—(CH$_2$)$_q$COOR$_{10}$ (wherein Ph is phenyl) yields the unsaturated ester of the Formula LII after workup. Careful reduction of this unsaturated ester by reaction with one equivalent of hydrogen over palladium-on-carbon in alcohol yields the saturated ester of the Formula LIII. The free acid or a pharmacologically acceptable salt of this ester is prepared by means well known in the art. The corresponding amides, phenacyl esters, and the like are prepared by the methods depicted in e.g., U.S. Pat. Nos. 4,292,445 and 4,172,206.

The dihydrobenzofurans are prepared as depicted in Chart E. A solution of a formula LX benzofuran in water is stirred with excess sodium amalgam (NaHg) for 24 hr. After workup there is obtained the corresponding Formula LXI dihydrobenzofuran. (See, e.g., D. T. Witiak, et al., J. Med. Chem. 14, 754 (1971).)

Reduction of the corresponding acid or ester of the formula COOR$_{10}$ with lithium aluminum hydride as depicted in Chart C, (XL to XLI) is used to prepare all of the corresponding alcohols within the scope of Formula I. Conversion of the alcohol to a corresponding acid addition salt is accomplished by known means.

The compounds of this invention wherein m is zero and $R_7$ is hydrogen are prepared by the method of Chart F, which is described more fully in Preparation 25 and Example 26. A formula LXXV aldehyde is reacted with an appropriate Wittig reagent (prepared by reacting sodium hydride and dimethylsulfoxide with an alkoxyalkyltriphenyl phosphonium halide) to yield the formula LXXVI enol ether. This compound is treated with perchloric acid to yield the formula LXXVII benzofuran.

Compounds of this invention wherein $X_1$ is —O— or —S— are prepared by the method of Chart G. In Chart G, $X_5$ is —S— or —O—, and is attached at the 3 or 4 position of the pyridine ring. This procedure is described more fully in Preparations 4, 5, and 7 and Examples 2, 3, and 4. A compound of the formula LXXX (e.g., 3-hydroxypyridine) is treated with potassium hydroxide, and reacted with a compound of the formula LXXXI (e.g., p-bromoanisole) in the presence of activated copper bronze to yield the formula LXXXII product. The formula LXXXII compound is then reacted with hydrogen bromide to yield the formula LXXXIII product, which is then transformed to the corresponding benzofuran final products by the methods described above. The LXXXIII compounds wherein $X_5$ is —S— are similarly prepared by reaction of a 3 or 4-bromopyridine (LXXX') with p-methoxythiophenol (LXXXI) to yield the formula LXXXII compound.

Chart H depicts an alternate method for preparing the compounds of this invention. An ethyl-benzofuran-2-carboxylate of the formula XCVI is prepared from the corresponding XCV aldehyde by the methods described above. This compound is alkyl chlorinated by treatment with paraformaldehyde and zinc chloride to yield the formula XCVII compound. This compound is formylated by known methods, (e.g., reaction of sodium metal with ethanol followed by the addition of the XCVII compound) to yield the formula XCVIII compound. The formula XCVIII compound is reacted with 3-amino pyridine to yield the compound of the formula C wherein $X_1$ is —NH—. This is described in Example 3. The formula XCVII compound is also treated with a mixture of sodium hydride, dimethylformamide, and 3-hydroxypyridine to obtain the formula CII compound wherein $X_1$ is —O—.

Chart I depicts a method for preparing chloro-pyridinyl compounds of this invention. The CV pyridinyl derivative is treated with m-chloroperbenzoic acid to yield the corresponding CVI N-oxide. The N-oxide is treated with phosphorous oxychloride to yield the corresponding chloropyridyl isomers of the formula CVII.

Substituted benzofurans (i.e. compounds wherein $R_9$ and $R_{12}$ are other than hydrogen) are prepared by the methods depicted in Charts J and K.

Chart J depicts a method for preparing brominated derivatives. An aldehyde of the formula CX (prepared by the method of Chart B, see formula (XXIV) is treated with bromine to yield the corresponding brominated compound of the formula CXI, which is then converted to the compounds of the present invention by the method of Chart A.

Chart K depicts a method for preparing methyl or methoxy substituted benzofurans or benzothiophenes. In Chart L, $R_{19}$ is methyl or methoxy. The formula CXV ether is hydrolyzed (using hydrobromic acid for example) to yield the formula CXVI alcohol. Similarly, the formula CXV' ether is hydrogenolyzed with hydrogen over palladium on carbon catalyst to yield the formula CXVI alcohol. This alcohol is treated with trifluoroacetic acid in the presence of hexamethylenetetramine to yield the formula CXVII aldehyde, which is converted to the compounds of this invention by the method of Chart A.

Various substituted hydroxy benzaldehydes are available commercially or may be prepared by methods known in the art. The hydroxybenzaldehydes are thus converted to the claimed benzofurans by the method of Chart A.

Compounds where $Z_1$ is 4-methylpyridine are prepared by converting the corresponding 4-chloropyridine of Chart J with methyl magnesium halides to the 4-methyl pyridine derivative according to the procedure described in K. Thomas and D. Jerchel, in "Newer Methods of Organic Chemistry," Vol. III., W. Foerst, ed., Academic Press, N.Y. 1964, pp 74–75.

The 4-methoxy, 4-amino, and 4-N,N-dimethylamino derivatives are prepared from the corresponding 4-methoxy-3-bromopyridine (see T. Talik, Roczniki Chem, 36:1465 (1962)), 3-bromo-4-aminopyridine (see T. Talik, Roczniki Chem., 37:69 (1963)) and 3-bromo-4-dimethylaminopyridine (see J. M. Essery and K. Schofield, J. Chem. Soc., 4953 (1960)), respectively, using the procedure of Chart I (conversion of XCVIII to CI).

Preparation of various other benzofuran derivatives within the scope of this invention are prepared by analogous procedures well known in the art.

Certain compounds of the present invention are preferred. Thus, compounds of the formula I, wherein D denotes a double bond, $X_1$ is —O—, $Z_1$ is 3-pyridinyl, m is zero, $R_7$ is $COOR_1$, $R_1$ is Na or H and $R_9$ and $R_{12}$ are hydrogen are preferred. Compounds having all these preferences are more preferred. Thus, sodium 5-(3'-pyridinyloxy)benzofuran-2-carboxylate is the most preferred compound of this invention.

DESCRIPTION OF THE PREFERRED EMBODIMENTS

The present invention is seen more fully by the Examples given below.

Preparation 1

Ethyl Benzofuran-2-carboxylate

Refer to Chart H (conversion of XCV to XCVI).

A 3-neck round bottomed flask equipped with a mechanical stirrer, a dropping funnel, a gas inlet tube, and a thermometer is charged with 24.4 g (0.2 mol) of salicyl aldehyde (Aldrich) and 800 ml of THF-EtOH (19:1) under a nitrogen atmosphere. To this solution 150 ml (0.24 mol) of potassium t-butoxide in THF (1.6M) is added dropwise over 20 min at room temperature. A milky yellow precipitate is formed during the addition. The mixture is stirred at room temperature for one hr. A solution of 57.4 g (0.24 mol) of diethyl bromomalonate (Aldrich) in 20 ml of THF is added dropwise over 10 min. The mixture becomes grayish in color. After stirring for one hr at room temperature, another portion of potassium t-butoxide in THF (150 ml, 0.24 mol) is added dropwise over 40 min at room temperature. TLC shows no starting material remaining after an additional 40 min of stirring. The mixture is poured into 500 ml of brine mixed with crushed ice and extracted twice with ethyl acetate (1 L). The organic phase is washed with brine and dried over anhydrous magnesium sulfate. Filtration and concentration affords a deep brown oil. Vacuum distillation affords pure ethyl benzofuran-2-carboxylate (boiling point 88°–91° C./0.03 mm, 32.5 g, 85%).

The NMR (CDCl$_3$; TMS, δ) spectrum reveals peaks at 7.85–7.22, 4.42, and 1.40.

The IR spectrum (film, $\nu_{max}$) reveals peaks at 1720, 1575, 1560, 1480, 1180, 1140, 1090, 1010, 950, 890, 840, and 750 cm$^{-1}$.

The mass spectrum reveals an ion at m/e 190.0622.

The C:H ratio is 69.24:5.32.

PREPARATION 2

Ethyl 5-chloromethylbenzofuran-2-carboxylate and Ethyl 4-chloromethylbenzofuran-2-carboxylate Refer to Chart H (conversion of XCVI to XCVII).

A 250 ml 3-neck (24/40) round bottomed flask, equipped with a magnetic stirring bar, a condenser and a gas bubbler, is charged with a solution of 32.13 g (0.169 mol) of ethyl benzofuran-2-carboxylate (Preparation 1) dissolved in 85 ml of chloroform. Paraformaldehyde (6.7 g, 0.22 mol) and zinc chloride (6.1 g, 0.045 mol) (dried at 100° C. under vacuum for 2 days) are added. The resulting mixture is heated to 50° C. and anhydrous hydrogen chloride gas is bubbled slowly through the magnetically stirred mixture. The mixture gradually turns black in color and after stirring for 4 hrs TLC analysis indicates only about a 50% conversion to the titled products. Another 6.7 g of paraformaldehyde (0.22 mol) is added and the resulting mixture is stirred for an additional hr. Little change in the course of the reaction is observed by TLC. The mixture is cooled, diluted with chloroform and washed consecutively with water, saturated aqueous sodium bicarbonate and brine. Drying (MgSO$_4$), filtration and concentration afford 40.98 g of crude product mixture as a dark brown oil.

This mixture is chromatographed on a column containing 1.5 kg of silica gel 60 eluting with Skellysolve B-ethyl acetate (19:1) fractions 7–13 afford unreacted starting material (10.6 g, 33%) (fractions 1–9, 1000 ml; fractions 10–13, 400 ml). Fractions 15–29 (400 ml) contained a mixture of the desired products ethyl 5- (and 4-)chloromethyl-benzofuran-2-carbonylate (18.2 g, 45%) and fractions 30–47 (400 ml) afford 2.1 g (4.3%) of ethyl 4,5-bischloromethylbenzofuran-2-carboxylate.

The NMR (CDCl$_3$; TMS, δ) spectrum reveals peaks at 7.82–7.10, 4.82, 4.45, and 1.40.

The IR (film, $\nu_{max}$) spectrum reveals peaks are observed at 2970, 1720, 1570, 1470, 1440, 1370, 1320, 1300, 1230, 1190, 1140, 1005, 945, 770, 750, 700, and 620 cm$^{-1}$.

The mass spectrum reveals ions at m/e 238.0384, 204, 193, 175, 159, 131, and 102. (The methyl ester of this compound is also disclosed in U.S. Pat. No. 2,754,286).

PREPARATION 3

Ethyl 5-formylbenzofuran-2-carboxylate and Ethyl 4-formylbenzofuran-2-carboxylate Refer to Chart H (conversion of XCVII to XCVIII).

To 10 ml of absolute ethanol under a nitrogen atmosphere is added 0.40 g (17.4 mmol) of sodium metal in small pieces over 2–3 min. When gas evolution has ceased and all of the sodium has dissolved, 2-nitropropane (1.55 ml, 16.2 mmol) is added via syringe in one portion. Almost immediately a white precipitate forms which stops the stirring bar. This is broken up by a spatula to give a milky suspension. The resulting magnetically stirred mixture is heated to 65° C. for 30 min under a nitrogen atmosphere. To this mixture is added a solution of the starting material dissolved in 20 ml of absolute ethanol. After stirring at 65° C. for 3 hr TLC analysis indicates only a trace of starting material remaining. The reaction is quenched by the addition of saturated aqueous ammonium chloride and ethanol is removed under reduced pressure. The concentrate is diluted with 25 ml of brine and extracted with chloroform (75 ml). This results in an emulsion which can not be broken up. Consequently this mixture is filtered through a Celite pad and the filtrate is diluted with 25 ml brine and equilibrated. The organic layer is drawn off and the aqueous wash is extracted twice with 50 ml portions of chloroform. The organic layers are combined, dried (MgSO$_4$), filtered and concentrated to give 3.19 g of crude titled product as a yellow oil.

The crude product is chromatographed on 192 g of HPLC grade silica gel eluting with hexane-acetone (6:1) and collecting 50 ml fractions. Fractions 10–12 contain a residual amount of unreacted starting material. Partial separation of the aldehyde isomers is observed. Fractions 13–15 afford primarily the 4-formyl isomers, fractions 16–18 give approximately a 1:1 mixture and fractions 19–24 give primarily the 5-formyl derivative. Altogher 2.26 g (77%) of a mixture of isomeric products is obtained. Fraction 19 (essentially pure ethyl 5-formyl-benzofuran-2-carboxylate) is set aside for analysis. This material later solidifies and is recrystallized from ethyl acetate/hexane to give white needles with a melting point of 101°–102° C.

The NMR (CDCl$_3$; TMS, $\delta$) spectrum reveals peaks at 10.20, 8.37–7.58, 4.50, and 1.47.

The IR (Nujol, $\nu_{max}$) spectrum reveals peaks at 1726, 1692, 1615, 1588, 1570, 1400, 1350, 1322, 1300, 1266, 1220, 1198, 1145, 1116, 1100, 1021, 949, 940, 919, 842, 834, 781, 767, 750 and 683 cm$^{-1}$.

The mass spectrum reveals ions at m/e 218.0588, 203, 189, 173, 161, 146, and 117.

The C:H ratio is 66.03:4.64.

EXAMPLE 1

Ethyl 5-[(3'-pyridinyl)aminomethyl]-benzofuran-2-carboxylate and Ethyl 4-[(3'-pyridinyl)aminomethyl]-benzofuran-2-carboxylate (Formula I: Z$_1$ is 3-pyridinyl, X$_1$ is —NHCH$_2$— and is para to the oxygen, R$_9$ and R$_{12}$ are hydrogen, D is a double bond, m is zero)

Refer to Chart H (conversion of XCVIII to C).

Part A.

A 200 ml 1-neck (24/40) round bottomed flask is charged with 1.75 g (8.02 mmol) of the aldehyde mixture of Preparation 3, 3-aminopyridine (0.93 g, 9.8 mmol), p-toluenesulfonic acid (0.092 g, 0.48 mmol) and benzene (50 ml). The flask is fitted with a Dean-Stark trap and a condenser and the mixture is heated to reflux and stirred for 4 hr. Little change is observed by TLC after 2 hr. The mixture is cooled, filtered through a Celite pad and the filtrate is concentrated under reduced pressure to give a yellow oil.

Part B.

The oil is dissolved in 25 ml of methanol, placed under a positive nitrogen atmosphere, cooled to −25° C. and treated with 0.36 g (9.5 mmol) of sodium borohydride. After stirring at −25° C. for 20 min the reaction is quenched by the addition of saturated aqueous ammonium chloride and the methanol is removed under reduced pressure. The concentrate is diluted with 25 ml of saturated aqueous sodium bicarbonate and extracted with 100 ml of chloroform. The organic phase is washed with brine, (25 ml) dried (MgSO$_4$), filtered, and concentrated to give 2.60 g of crude product as a yellow oil.

This material is chromatographed on 192 g of HPLC grade silica gel, eluting with hexane-ethyl acetate (7:3) (+5% ethanol) and collecting 45 ml fractions. Fractions 37–46 are homogeneous by TLC and are combined and concentrated to give 0.48 g of the 4-pyridinylaminomethyl product as a pale yellow oil which solidifies. This material is recrystallized from chloroform/hexane to give a white grannular solid with melting point of 128.5–129. Fractions 47–51 contain a mixture of both isomers (0.22 g) and fractions 52–80 afford 1.46 g of the 5-pyridinylaminomethyl product as a white solid. This material is recrystallized from chloroform/hexane to give white needles with a melting point of 116°–117° C. The combined yield is 91%. For the 4-pyridinylamino compound, spectral data is as follows:

The NMR (CDCl$_3$; TMS, $\delta$) spectrum reveals peaks at 8.27–6.80, 5.19, 4.53, 4.37, and 1.38.

The IR (Nujol, $\nu_{max}$) spectrum reveals peaks at 3251, 1736, 1613, 1591, 1559, 1536, 1484, 1422, 1329, 1292, 1251, 1237, 1184, 1157, 1105, 1020, 846, 792, 763, 743, and 702 cm$^{-1}$.

The C:H:N ratio is 68.29:5.42:9.65.

The mass spectrum reveals ions at m/e 291.1170, 203 and 175.

For the 5-pyridinylamine product, spectral data is as follows:

The NMR (CDCl$_3$, $\delta$) spectrum reveals peaks at 8.20–6.82, 4.60–4.30, and 1.42.

The IR (Nujol, $\nu_{max}$) spectrum reveals peaks at 3239, 1726, 1714, 1591, 1581, 1531, 1420, 1346, 1295, 1231, 1220, 1200, 1141, 1123, 1089, 1026, 952, 896, 845, 799, 791, 764, 748, 705, 660 and 627 cm$^{-1}$.

The C:H:N ratio is 68.75:5.41:9.27.

The mass spectrum reveals ions at m/e 296.1156, 203, and 175.

EXAMPLE 2

Sodium 5-[(3'-pyridinyl)aminomethyl]-benzofuran-2-carboxylate (Formula I: Z$_1$ is 3-pyridinyl, X$_1$ is —NHCH$_2$— and is para to oxygen, R$_9$ and R$_{12}$ are hydrogen, D is a double bond, m is zero, Y$_1$ is —O—, and R$_7$ is —COONa)

The ethyl ester starting material (Example 1) (0.927 g, 3.11 mmol) is dissolved in 15 ml of absolute ethanol. Sodium hydroxide reagent (1.0 N, 3.11 ml, 3.11 mmol) is added and the resulting solution is stirred at room temperature for 2 hr at which time TLC analysis indicates no remaining starting material. Ethanol is removed under reduced pressure and the concentrate is diluted with 100 ml of water, filtered through a cotton plug, frozen and lyophilized to give 0.776 g of product as a pale yellow granular solid.

EXAMPLE 3

Sodium 4-[(3'-pyridinyl)aminomethyl]-benzofuran-2-carboxylate (Formula I: $Z_1$ is 3-pyridinyl, $X_1$ is —NHCH$_2$— and is meta to the oxygen, $R_9$ and $R_{12}$ are hydrogen, D is a double bond, m is zero, $Y_1$ is —O—, and $R_7$ is —COONa)

The ethyl ester starting material (Example 1) (0.208 g, 0.7 mmol) is dissolved in 10 ml, 0.700 ml, 0.7 mmol) is added and the resulting solution is stirred at room temperature for 1.5 hr. After this time TLC analysis still indicates unreacted starting material. Another 0.070 ml of sodium hydroxide reagent is added and the mixture (a precipitate had formed approximately 1 hr after the start of the hydrolysis) is stirred at room temperature for 65 hr a which time TLC analysis confirms the hydrolysis is complete. Ethanol is removed under reduced pressure and the concentrate is diluted with 50 ml of water, lyophilized to give 0.169 g of product as a white fluffy powder.

PREPARATION 4

3-(p-Methoxy)phenoxypyridine

Refer to Chart G (conversion of LXXX to LXXXII).

Following the procedure of Renshaw and Conn, J. Am. Chem. Soc. 59:297 (1937), a mixture of 10.95 g (0.166 mmol) of 85% potassium hydroxide pellets and 15.78 g (0.166 mmol) of 3-hydroxypyridine is heated to 200° C. in a three-necked round bottom flask equipped with a thermometer, distillation apparatus and air stirrer. The mixture first liquifies, then forms green crystals, presumably the potassium salt of 3-hydroxypyridine. The temperature is reduced to 150° C. and another 10 g (0.105 mmol) of 3-hydroxypyridine is added followed by 20.78 ml (0.166 mmol) of p-bromoanisole and 0.33 g of activated copper bronze (see below). The resulting mixture is heated to 200° C. and stirred for 2 hr. The brown solution is then cooled to 100° C. and poured into 300 ml of water. The solution becomes homogeneous (and black) after adding 39 g of 45% aqueous potassium hydroxide. The solution is transferred to a separatory funnel and the pH is adjusted to approximately 13. The final volume is 600 ml. Ethyl ether (8 L) is used to "extract" the compound: 500 ml of ether is added to the water layer and shaken, which results in an emulsion. The top 500 ml of the emulsion is extracted with ether until an organic layer can be discerned. The water layer after the ether extractions is then extracted with methylene chloride (4 L). The combined methylene chloride layers are washed with 500 ml of a pH=14 potassium hydroxide solution. The methylene chloride extracts and concentrate from the ether layers are combined and filtered through 3 inches of silica gel, thereby removing the maroon color. The organic layer is dried over magnesium sulfate and concentrated in vacuo to yield 13.3 g of residue which is distilled at 112° C. and 0.1–0.3 mm hg (lit. top 163°–164°/10 mm) to yield 10.05 g of product. The 3-hydroxypyridine, distills at approximately 60° C. and 0.1–0.3 mm Hg, and is therefore a slight contaminant (5%) in the final product.

The IR ($\nu_{max}$, mull) spectrum reveals peaks at 1230, 831, 1506, 1477, 1426, 1028, 709, 1261, 1103, 810, 824, 1191, 1199, 1574, and 1179 cm$^{-1}$. [Note: Continuous extraction of the water layer with methylene chloride would be much easier and more efficient than the laborious extraction procedure give above.]

The NMR (CDCl$_3$; TMS, δ) spectrum reveals peaks at 8.53–8.32, 7.74–6.82, and 3.80.

The mass spectrum reveals ions at m/e 201.0784, 202, 200, 188, 186, 173, 143, 123, 78, 77, 64, and 63.

TLC (silica gel GF) yields an $R_f$ of 0.11 (20% ethyl acetate/hexane).

Activation of copper bronze:

A suspension is prepared by adding 10 g of copper bronze to 120 ml of a 2% (by weight) iodine/acetone solution. The combination is stirred for 5–10 min, filtered, and the residue resuspended in 75 ml of a 1:1 concentrated hydrochloric acid/acetone solution. After stirring for 5 min the solution is filtered and the residue is washed with 25 ml of the 1:1 concentrated hydrochloric acid/acetone solution followed by acetone (3×100 ml). The resulting solid is dried in a dessicator under a vacuum for 1 hr.

PREPARATION 5

3-(p-Hydroxy)phenoxypyridine

Refer to Chart G (conversion of LXXXII to LXXXIII).

A solution of 9.0 g (44.7 mmol) of 3-(p-methoxy)-phenoxypyridine and 145 ml of 48% of hydrogen bromide is heated to reflux under a nitrogen atmosphere for 1.5 hr. The solution is cooled and concentrated in vacuo to dryness after which water is added (approximately 80 ml) and the resulting solution slowly added to saturated sodium bicarbonate (300 ml). The light pink, pH approximately equal to 9 solution is extracted with ethyl acetate (6×250 ml). The pH is adjusted to approximately 7 and again extracted twice with ethyl acetate (250 ml). The combined ethyl acetate layers are dried over magnesium sulfate; filtered, and concentrated in vacuo to yield a pink residue which is recrystallized in ethyl acetate/hexane to yield 6.82 g of product (82% of theory) with a melting point range of 131°–134° C.

The IR ($\nu_{max}$, mull) spectrum reveals peaks at 1232, 1507, 1427, 1260, 1482, 1198, 705, 843, 1575, 1457, 804, 627, 2677, 1110, and 3056 cm$^{-1}$.

The NMR (CDCl$_3$ and d$_6$-acetone; TMS) spectrum reveals peaks at δ 9.03–8.03, 8.52–8.27, 7.48–7.27, and 6.97.

The mass spectrum reveals ions at m/e 187.0633, 188, 186, 120, 109, 81, 79, 78, 65, and 51.

TLC (silica gel GF) yields an $R_f$ of 0.20 (40% ethyl acetate/hexane).

PREPARATION 6

2-Hydroxy-5-(3-Pyridinyloxy)benzaldehyde

Refer to Chart B (conversion of XXIII to XXIV).

A mixture of 1.00 g (5.34 mmol) of 3-(p-hydroxy)-phenoxypyridine and 0.79 g (5.61 mmol) of hexamethylenetetramine in 10 ml of trifluoroacetic acid is heated to 80° C. and is stirred under a nitrogen atmosphere for 4 hr. The reaction mixture is cooled to room temperature and the pH is adjusted to 7.5 with 50% aqueous sodium hydroxide, which results in an oily yellow precipitate. The solution is extracted with chloroform (3×250 ml, 1×100 ml) and the combined chloroform layers are dried over magnesium sulfate, filtered and concentrated in vacuo to yield 1.7 g of residue. The residue is chromatographed on 400 g of silica gel. The column is wet-packed and eluted with 6% acetone/methylene chloride and fractions of 20 ml are collected.

Fractions 54–83 are combined and concentrated in vacuo to yield 0.51 g of product. The product is recrystallized in ethyl acetate/hexane to give 0.31 g (27% of theory) with a melting point of 122°–124° C.

The IR ($\nu_{max}$ (mull)) spectrum reveals peaks at 1672, 1232, 1446, 1441, 1246, 1430, 1479, 1276, 1267, 902, 1148, 806, 699, 1578, and 1382 cm$^{-1}$.

The NMR (CDCl$_3$; TMS, $\delta$) spectrum reveals peaks at 9.97, 8.60–8.30, and 7.50–6.80.

The mass spectrum reveals ions at m/e 215.0582, 216, 214, 169, 137, 79, 78, 53, 51, and 39.

TLC (silica gel GF) yields an R$_f$ of 0.20 (6% acetone/methylene chloride).

EXAMPLE 4

5-(3-Pyridinyloxy)benzofuran-2-carboxylic acid, ethyl ester (Formula I: $Z_1$ is 3-pyridinyl, $X_1$ is —O— and is para to the oxygen, $R_9$ and $R_{12}$ are hydrogen, D is a double bond, m is zero, and $R_7$ is —COOCH$_2$CH$_3$)

To a mechanically stirred solution of 0.74 g (18.6 mmol) of sodium hydride (60% oil dispersion) in 60 ml of dry benzene under a nitrogen atmosphere is added 1.0 g (4.65 mmol) of hydroxy aldehyde of Preparation 6 in one portion. The mixture is stirred for 15 min before adding 1.31 ml of diethyl bromomalonate in one portion. A spatula tip of dicyclohexano-18-crown-6-ether is added and the reaction is stirred at room temperature under a nitrogen atmosphere for 40 hr. The color changes from grey-green to dark yellow. The mixture is poured into 300 ml of 1:1 saturated brine/sodium bicarbonate solution, shaken, then extracted with ethyl acetate (3×250 ml). The ethyl acetate layers are dried over magnesium sulfate, filtered, and concentrated in vacuo to yield 2.2 g of residue. The material is chromatographed on 220 g of silica gel. The column is wet-packed and eluted with 10% isopropanol/hexane and fractions of 20 ml were collected. Fractions 54–89 are combined and concentrated to yield 0.59 g of product. This product is recrystallized in ethyl ether/hexane at 0° C. The crystals are filtered and washed with cold hexane and dried in vacuo to yield 0.38 g of product (29% of theory) with a melting point pf 69°–70° C.

The IR ($\nu_{max}$ (mull)) spectrum reveals peaks at 1725, 1195, 1145, 1233, 1426, 1318, 1273, 1565, 1184, 1265, 1575, 1220, 1474, 1209, and 1102 cm$^{-1}$.

The NMR (CDCl$_3$; TMS, $\delta$) spectrum reveals peaks at 8.63–8.30, 7.80–6.97, 4.67–4.23, and 1.67–1.20.

The mass spectrum reveals ions at m/e 283.0844, 284, 255, 254, 239, 238, 211, 182, 154, and 78.

TLC (silica gel GF) yields an R$_f$ of 0.24 (10% isopropanol/hexane).

EXAMPLE 5

5-(3-Pyridinyloxy)benzofuran-2-carboxylic acid, sodium salt (Formula I: $Z_1$ is 3-pyridinyl, $X_1$ is —O— and is para to the oxygen, $R_9$ and $R_{12}$ are hydrogen, D is a double bond, m is zero, and $R_7$ is —COONa)

A solution of 0.10 g (0.33 mmol) of ethyl ester of Example 4 in 7 ml of methanol and 3.53 mol of 0.100 M sodium hydroxide is stirred at room temperature under a nitrogen atmosphere for 16 hr. The reaction mixture is filtered through a fine porosity funnel and the filtrate is concentrated in vacuo to dryness. The resulting residue is triturated with acetonitrile for 0.5 hr, filtered and the solids washed with cold acetonitrile. The solids are dried in vacuo to yield 63 mgs of product (68% of theory) with a melting point greater than 300° C.

The IR ($\nu_{max}$ (mull)) spectrum reveals peaks at 1601, 1409, 1565, 1378, 1451, 1253, 1229, 1190, 791, 1476, 1334, 1272, 3029, 1145, 3056 cm$^{-1}$.

PREPARATION 7

4-(3-Pyridinylthio)phenol and the corresponding methyl ether

Refer to Chart G (conversion of LXXX' to LXXXII' and LXXXIII).

A 1000 ml, 3-necked, round-bottomed flask, fitted with air stirrer, a condenser and nitrogen inlet, is flame-dried, then recooled in an atmosphere of nitrogen. A stirred, cooled (0°) solution of 14.0 g (100 mmol) of p-methoxythiophenol (freshly distilled) in 200 ml of hexamethylphosphoramide is treated with 17.62 g of a 22.7% oil dispersion of potassium hydride (100 mmol), added in portions over 10 min via a wide-mouthed pipet (with vigorous hydrogen evolution). After the potassium hydride addition is complete, the cooling bath is removed, and the orange mixture is stirred for 15 min at 25° (hydrogen evolution has ceased). 3-Bromopyridine (15.8 g, 100 mmol) is added without solvent, and the homogeneous brown mixture is stirred at 80° for 24 hr in a nitrogen atmosphere. The reaction mixture (very dark) is cooled to 5°, poured into 1:1 brine/water (1 l), adjusted to pH 7 with 2M hydrochloric acid and extracted with ethyl acetate (5×400 ml). The extracts are washed with water (5×300 ml) and brine, dried over anhydrous magnesium sulfate and concentrated in vacuo.

The crude product (36 g) is chromatographed on 3 kg of silica gel. The column is packed with 10% acetone/methylene chloride, then eluted with 20 l of 10%, 8 l of 20% and 8 l of 40% acetone/methylene chloride.

Fractions 30–69, combined based on their TLC homogenity, affords 6.81 g of title compound methyl ether (31% of theory), a pale yellow oil.

The IR ($\nu_{max}$, neat) spectrum reveals peaks at 3000, 2940, 2830, 1590, 1550, 1490, 1460, 1440, 1400, 1285, 1245, 1170, 1100, 1025, 1015, 825, 795, and 700 cm$^{-1}$.

The NMR (CDCl$_3$; TMS, $\delta$) spectrum reveals peaks at 8.43–8.34, 7.48–6.84 and 3.82.

The mass spectrum reveals ions at m/e 217.0579, 202, 173, 131, 130, 96, 78, 63, 51, and 39.

TLC (silica gel GF) yields an R$_f$ of 0.40 (10% acetone/methylene chloride).

Fractions 109–128 from the above chromatogram are combined and yield 5.3 g of 4-(3-pyridinylthio)phenol (26% of theory). This material crystallizes readily and, after trituration with ether, affords white crystals with melting point 149°–151°.

The IR ($\nu_{max}$, (mull)) spectrum reveals peaks at 3083, 3068, 2791, 2766, 2726, 2672, 1601, 1582, 1557, 1498, 1471, 1460, 1455, 1410, 1285, 1248, 1237, 1171, 1038, 1025, 836, 798, and 702 cm$^{-1}$.

The NMR (CDCl$_3$; TMS, $\delta$) spectrum reveals peaks at 9.40, 8.35–8.06, and 7.41–6.75.

The mass spectrum reveals ions at m/e 203.0416, 186, 174, 159, 142, 125, 115, 97, 78, and 51.

TLC (silica gel GF) yields an R$_f$ of 0.19 (10% acetone/methylene chloride).

Demethylation of title compound methyl ether

A solution of 6.6 g of methyl ether (fractions 30–69 above) in 80 ml of concentrated hydrobromic acid is heated at reflux for one hr. The hydrobromic acid is then removed on the rotary evaporator (high vacuum pump, 40°). The residue was dissolved in 1:1 brine/water, adjusted to pH 7.0–7.2, and extracted thoroughly with ethyl acetate. The extracts were washed with brine, dried over anhydrous magnesium sulfate and concentrated. The crude product crystallizes spontaneously and is about 95% pure 4-(3-pyridinylthio)phenol by TLC. Recrystallization from acetone/methylene chloride, or from ether, does not substantially decrease the amount of two minor move polar impurities. The crude product is sufficiently clean to be used in subsequent reactions.

PREPARATION 8

2-Hydroxy-5-(3-pyridinylthio)benzaldehyde

Refer to Chart B (conversion XXIII to XXIV).

A solution of 4.06 g (20 mmol) of 4-(3-pyridinylthio)-phenol and 2.94 g (21 mmol) of hexamethylenetetramine in 40 ml of trifluoroacetic acid is heated at 80° under a nitrogen atmosphere for 5.5 hr. The mixture is cooled to 35° and concentrated in vacuo (rotovac-high vacuum pump). The residue is diluted with 150 ml of water and allowed to stand at 25° for 30 min. The pH of the aqueous mixture is then adjusted to 7.0, and the product is isolated by extraction with ethyl acetate. The extracts are washed with brine, dried over magnesium sulfate, and evaporated.

The crude product (6.5 g), mostly two components in comparable amounts, is chromatographed on a column containing 900 g of silica gel. The column is packed with 10% acetone/methylene chloride and eluted (1×300 ml, then 25 ml fractions) with 4 l of 10%, 4 l of 20% and 6 l of 30% acetone/methylene chloride.

Fractions 98–169 were combined and yielded 1.99 g of the title aldehyde, homogeneous by TLC (43% of theory). Recrystallization of a 200 mg sample from ethyl acetate/hexane gives 160 mg of a white solid with melting point of 115°–117° C.

The IR ($\nu_{max}$ (mull)) spectrum reveals peaks at 1680, 1673, 1592, 1579, 1560, 1491, 1475, 1425, 1413, 1393, 1301, 1234, 1175, 167, 1111, 1043, 800, 787, 697, and 638.

The NMR (CDCl$_3$; TMS, δ) spectrum reveals peaks at 11.08, 9.98, 8.65–8.40 and 7.90–7.03. The mass spectrum reveals ions at m/e 231.0366, 203, 185, 174, 153, 142, 121, 111, 97, 79, 63, 51, and 39.

TLC (silica gel GF) yields an R$_f$ of 0.39 (15% acetone/methylene chloride).

Fractions 202–226 yield 180 mg of clean starting material (4%).

Fractions 346–400 from the above chromatogram are combined and afford 1.70 g of a colorless oil, whose identify remains uncertain. This by-product is completely stable to 5% trifluoroacetic acid in water and hence is likely not the methyl imine corresponding to the title aldehyde. (Such an intermediate can be isolated if hydrolysis conditions are too mild.) This material possesses no carbonyl band in the IR but has an unidentified singlet worth 2–3H at 4.05 ppm. (Still a phenol.)

EXAMPLE 6

5-(3-Pyridinylthio)-benzofuran-2-carboxylic acid, ethyl ester (Formula I: $Z_1$ is 3-pyridinyl, $X_1$ is —S— and is para to the oxygen, $R_9$ and $R_{12}$ are hydrogen, D is a double bond, m is zero, and $R_7$ is —COOCH$_2$CH$_3$)

To a solution of 1.23 g (30.8 mmol) of sodium hydride (60% oil dispersion) in 80 ml of benzene under a nitrogen atmosphere with mechanical stirring is added 1.78 g (7.7 mmol) of hydroxyaldehyde from the preceding experiment in one portion, followed by 1.23 ml (7.2 mmol) of diethyl bromomalonate. A spatula tip of dicyclohexane-18-crown-6 is added and the reaction is stirred for 24 hr. After this time, another 1.23 ml (7.2 mmol) of diethyl bromomalonate is added and after 20 hr another 0.25 g (6.25 mmol) of sodium hydride (60% oil dispersion) is added to the reaction mixture. The reaction progress is periodically monitored by thin layer chromatography. After 3 days of stirring under nitrogen another 0.25 g (6.25 mmol) of sodium hydride (60% oil dispersion) is again added and after 30 hr the reaction mixture is poured into 250 ml of dry tetrahydrofuran and the resulting solution is stirred at room temperature under a nitrogen atmosphere for 36 hr. Another 0.2 g (5.0 mmol) of sodium hydride (60% oil dispersion) is added again and after 40 hr stirring under a nitrogen atmosphere the solution is concentrated in vacuo to remove ½ of the tetrahydrofuran. The resulting solution is poured into a stirred brine/ice misture and the pH is continuously monitored and adjusted with dilute hydrochloric acid so as to keep it below 10. After complete addition of the reaction mixture the pH is adjusted with ethyl acetate (3×250 ml). The pH is changed to 7 and the solution is extracted with chloroform (250 ml). The combined ethyl acetate extracts are dried over magnesium sulfate, filtered and concentrated in vacuo. The residue is dissolved in the chloroform wash which is dried over magnesium sulfate, filtered and concentrated in vacuo to yield 4.7 g of residue. The residue is chromatographed on 325 g of silica gel. The column is wet-packed and eluted with 50% ethyl acetate/hexane and fractions of 30 ml were collected. Fractions 31–41 were combined and concentrated in vacuo to yield 0.67 g of oil products (29% of theory). The oil is dried under a vacuum for 16 hr. Part of the product which crystallized slowly on standing was recrystallized in diethyl ether/hexane to yield yellow crystals with a melting point range of 59°–61° C.

The NMR (CDCl$_3$; TMS, δ) spectrum reveals peaks at 8.55–8.30, 7.85–7.00, 4.58–4.31, and 1.51–1.33.

The mass spectrum reveals ions at m/e 299.0616, 300, 271, 270, 254, 244, 226, 215, 198, 176, 148, 130, 120, 92, 74, and 47.

TLC (silica gel GF) yields an R$_f$ of 0.36 (50% ethyl acetate/hexane).

EXAMPLE 7

5-(3-Pyridinylthio)-benzofuran-2-carboxylic acid, sodium salt (Formula I: $Z_1$ is 3-pyridinyl, $X_1$ is —S— and is para or ortho to the oxygen, $R_9$ and $R_{12}$ are hydrogen, D is a double bond, m is zero, and $R_7$ is —COONa)

To a solution of 0.200 g (0.63 mmol, assumed 95% purity) of the ester of Example 6 in 8 ml of tetrahydrofuran is added 6.34 ml of 0.700 M sodium hydroxide. The reaction mixture stirred under a nitrogen atmosphere for 3 days. The solution is concentrated to dryness using a vacuum pump and the resulting residue is triturated with 8 ml of acetonitrile for 4 hr. The crystals are filtered and washed with acetonitrile and then dried under vacuum to yield 0.144 g of product (77% of theory) with a melting point greater than 300° C.

TABLE I

FORMULA

TABLE I-continued
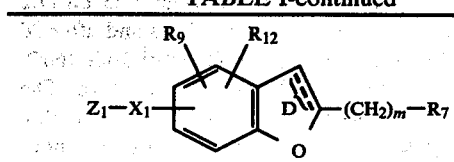
CHART A
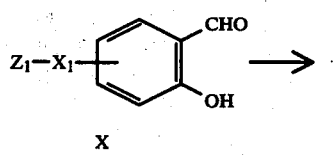
X
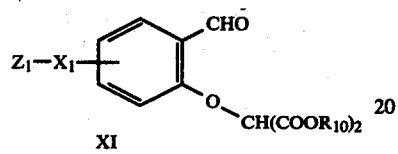
XI
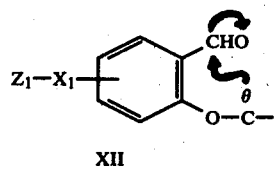
XII
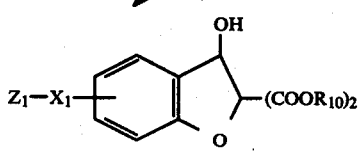
XIII
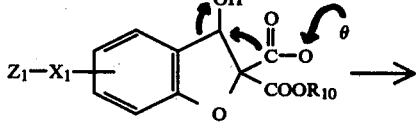
XIV
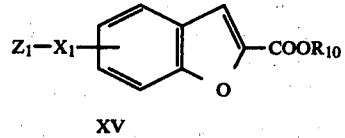
XV
CHART B
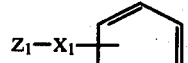
XX
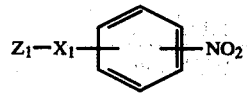
XXI
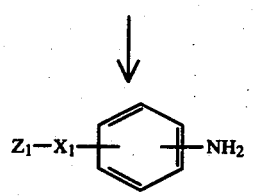
XXII
XXIII
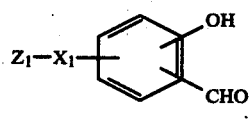
XXIV
CHART C
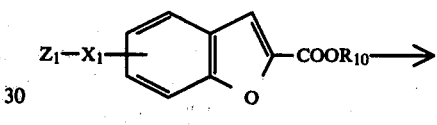
XL
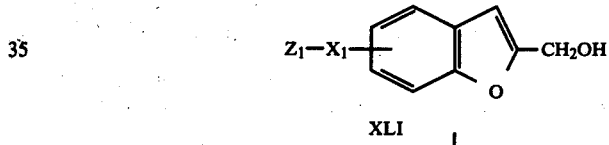
XLI
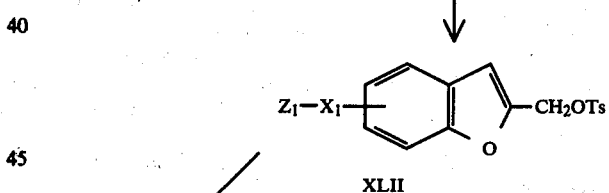
XLII
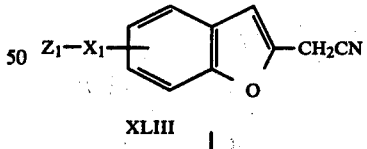
XLIII
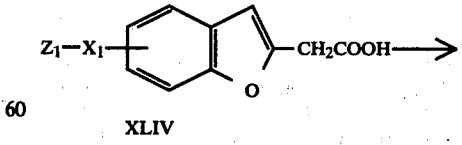
XLIV
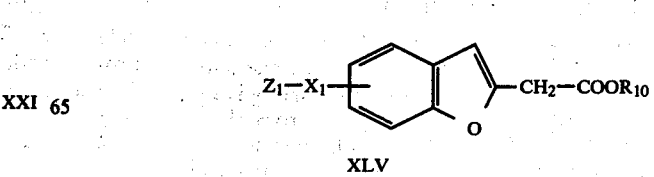
XLV TABLE I-continued
CHART D
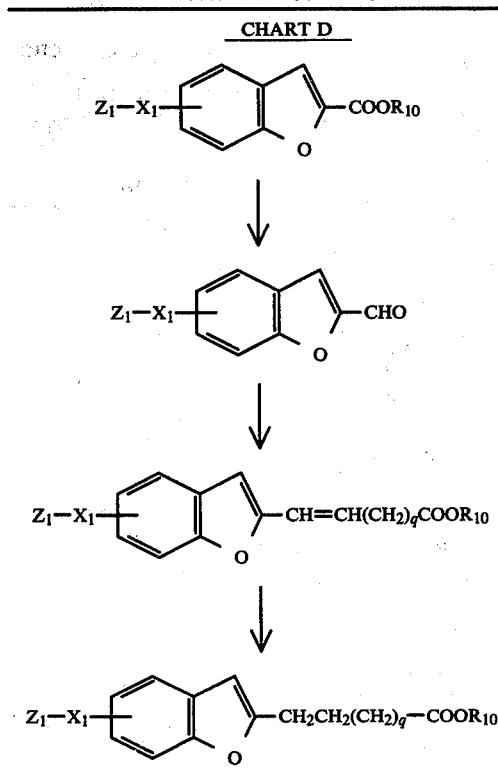
CHART E
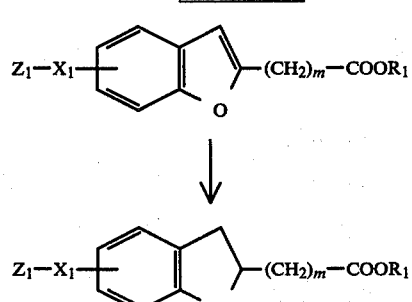
CHART F
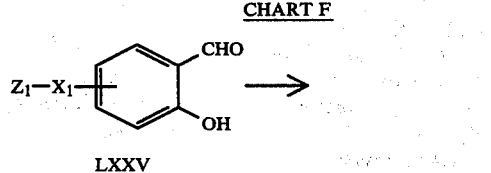
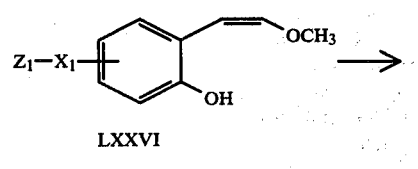
CHART G
TABLE I-continued
L
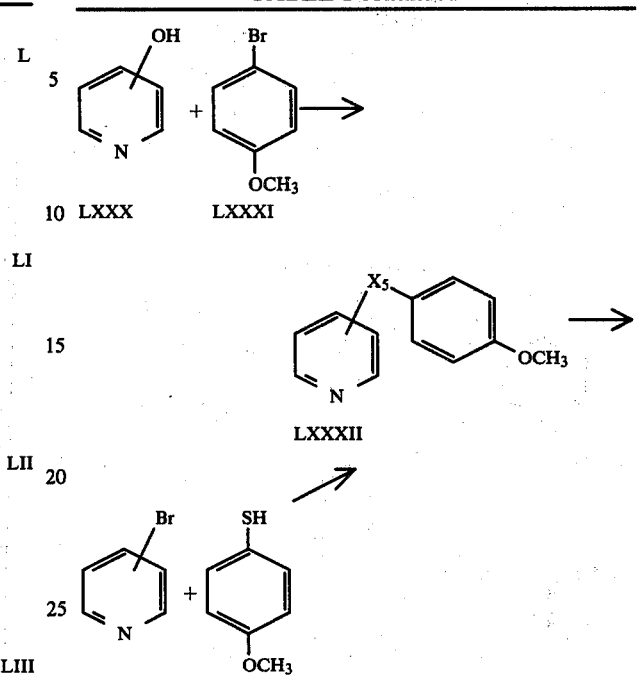
LXXX    LXXXI
LI
LII
LIII
LX
CHART H
LXI
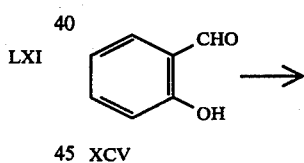
XCV
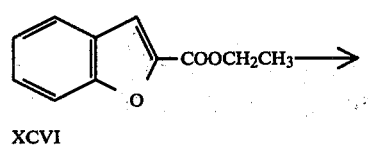
XCVI
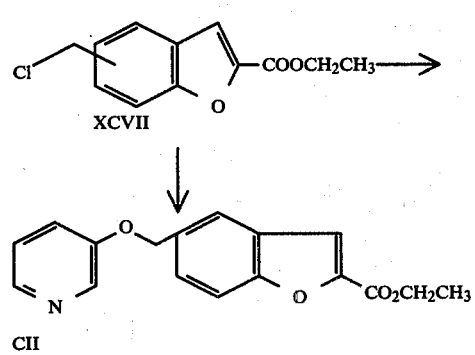
XCVII
CII TABLE I-continued

XCVIII

↓

C

CHART I

CV →

CVI →

CVII →

CHART J

CX (XXIV, Chart B) → CXI

CHART K

CXV → CXVI ↓

TABLE I-continued

CXV' CXVII

I claim:
1. A compound of the formula I:

I wherein $Z_1$ is
  (a) 4-pyridinyl,
  (b) 3-pyridinyl,
  (c) 3-pyridinyl substituted at the 4 position by
    (1) methyl,
    (2) —OCH$^3$,
    (3) —N(CH$_3$)$_2$, or
    (4) —NH$_2$, or
  (d) 3-pyridinyl substituted at the 2, 4, 5, or 6 position by chlorine;
wherein $X_1$ is
  (a) —O—,
  (b) —S—,
  (c) —S(O)—,
  (d) —S(O)$_2$—,
  (e) —CH$_2$—N(R$_3$)—, or
  (f) —N(R$_3$)—CH$_2$—,
wherein $R_1$ is hydrogen, a pharmacologically acceptable cation, (C$_1$-C$_{12}$) alkyl, (C$_3$-C$_{10}$) cycloalkyl, (C$_7$-C$_{12}$) aralkyl, phenyl, phenyl mono-, di-, or trisubstituted by chloro, (C$_1$-C$_3$) or alkyl, or phenyl para-substituted by
  (a) —NHCO—R$_{25}$,
  (b) —O—CO—R$_{26}$,
  (c) —CO—R$_{24}$,
  (d) —O—CO—(p—Ph)—R$_{27}$, or
  (e) —CH=N—NH—CO—NH$_2$,
wherein R$_{24}$ is phenyl or acetamidophenyl, R$_{25}$ is methyl, phenyl, acetamidophenyl, benzamidophenyl, or amino, R$_{26}$ is methyl, phenyl, amino or methoxy; and R$_{27}$ is hydrogen or acetamido, and wherein —(p-Ph) is 1,4-phenylene;
wherein $R_3$ is
  (a) hydrogen or
  (b) (C$_1$-C$_3$)alkyl;
wherein $R_4$ is
  (a) hydrogen,
  (b) (C$_1$-C$_4$)alkyl, or
  (c) phenyl;
wherein $R_7$ is
  (a) hydrogen,
  (b) —CH$_2$OH,
  (c) —COOR$_1$,
  (d) —CH$_2$N(R$_4$)$_2$,
  (e) —CN
  (f) CON(R$_4$)$_2$, or
  (g) —C(O)—R$_4$;

wherein $R_9$ and $R_{12}$ are the same or different and are
  (a) hydrogen,
  (b) $(C_1-C_4)$alkyl
  (c) fluoro
  (d) chloro,
  (e) bromo,
  (f) —$OCH_3$, or,
  (h) when taken together and attached to contiguous carbon atoms, —O—$CH_2$—O—;
wherein D represents a single or a double bond; and
wherein m is an integer from 0 to 4, inclusive; including pharmacologically acceptable acid addition salts thereof; and
when D represents a single bond, an enantiomer or a racemic mixture of enantiomers thereof.

2. A compound of claim 1, selected from the group consisting of:
ethyl 5-[(3'-pyridinyl)aminomethyl]-benzofuran-2-carboxylate,
ethyl 4-[(3'-pyridinyl)aminomethyl]-benzofuran-2-carboxylate,
sodium 5-[(3'-pyridinyl)aminomethyl]-benzofuran-2-carboxylate,
sodium 4-[(3'-pyridinyl)aminomethyl]-benzofuran-2-carboxylate,
5-(3-pyridinyloxy)benzofuran-2-carboxylic acid, ethyl ester,
5-(3-pyridinyloxy)benzofuran-2-carboxylic acid, sodium salt,
5-(3-pyridinylthio)-benzofuran-2-carboxylic acid, ethyl ester, and
5-(3-pyridinylthio)-benzofuran-2-carboxylic acid, sodium salt.

3. Ethyl 5-[(3'-pyridinyl)aminomethyl]-benzofuran-2-carboxylate, a compound of claim 2.

4. Ethyl 4-[(3'-pyridinyl)aminomethyl]-benzofuran-2-carboxylate, a compound of claim 2.

5. Sodium 5-[(3'-pyridinyl)aminomethyl]-benzofuran-2-carboxylate, a compound of claim 2.

6. Sodium 4-[(3'-pyridinyl)aminomethyl]-benzofuran-2-carboxylate, a compound of claim 2.

7. 5-(3-Pyridinyloxy)benzofuran-2-carboxylic acid, ethyl ester, a compound of claim 2.

8. 5-(3-Pyridinyloxy)benzofuran-2-carboxylic acid, sodium salt, a compound of claim 2.

9. 5-(3-pyridinylthio)-benzofuran-2-carboxylic acid, ethyl ester, a compound of claim 2.

10. 5-(3-Pyridinylthio)-benzofuran-2-carboxylic acid, sodium salt, a compound of claim 2.

* * * * *

UNITED STATES PATENT OFFICE
CERTIFICATE OF CORRECTION

Patent No. 4,455,427                    Dated 19 June 1984

Inventor(s) Roy A. Johnson

It is certified that error appears in the above-identified patent and that said Letters Patent are hereby corrected as shown below:

Column 2, line 22, "...-(p-Rh)-$R_{27}$, or" should read -- ...-(p-Ph)-$R_{27}$, or.

Column 2, line 53, "togetner" should read -- together --.

Column 18, line 43, "..., 130, 120, 92, ..." should read -- ..., 130, 120, 102, 92, ...--.

Signed and Sealed this

Twenty-fifth Day of June 1985

[SEAL]

Attest:

DONALD J. QUIGG

Attesting Officer     Acting Commissioner of Patents and Trademarks